United States Patent [19]

Nakayama et al.

[11] Patent Number: 4,702,764

[45] Date of Patent: Oct. 27, 1987

[54] CARBAMOYLTRIAZOLES, AND THEIR PRODUCTION AND USE

[75] Inventors: Koji Nakayama, Osaka; Ryo Yoshida, Kawanishi; Kouichi Morita, Toyonaka, all of Japan

[73] Assignee: Sumitomo Chemical Company, Limited, Osaka, Japan

[21] Appl. No.: 656,885

[22] Filed: Oct. 2, 1984

[30] Foreign Application Priority Data

Oct. 18, 1983 [JP] Japan ................................. 58-194603

[51] Int. Cl.$^4$ ................. C07D 249/12; A01N 43/653
[52] U.S. Cl. ......................................... 71/92; 548/265
[58] Field of Search ................ 548/265; 260/245.5; 546/210; 71/92

[56] References Cited

U.S. PATENT DOCUMENTS

| | | | |
|---|---|---|---|
| 3,308,131 | 3/1967 | McKusick | 548/265 |
| 3,952,001 | 4/1976 | Brookes et al. | 548/265 |
| 4,201,565 | 6/1980 | O'Neal | 71/92 |
| 4,217,129 | 8/1980 | Shepard et al. | 71/92 |
| 4,255,435 | 3/1981 | Watkins et al. | 548/265 |
| 4,280,831 | 7/1981 | Patel | 548/265 |
| 4,363,915 | 12/1982 | Patel | 548/265 |

*Primary Examiner*—Glennon H. Hollrah
*Assistant Examiner*—D. L. Dinner
*Attorney, Agent, or Firm*—Birch, Stewart, Kolasch & Birch

[57] ABSTRACT

A compound of the formula:

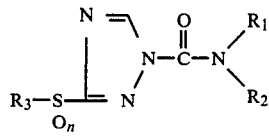

wherein $R_1$ and $R_2$ are each a lower alkyl group or they may together represent a lower alkylene group so as to form a nitrogen-containing cyclic group with the nitrogen atom to which they attach, $R_3$ is a cycloalkyl(lower)alkyl group, an oxacycloalkyl(lower)alkyl group or a dioxacycloalkyl(lower)alkyl group and n is an integer of 0 to 2, which is useful as a herbicide.

5 Claims, No Drawings

CARBAMOYLTRIAZOLES, AND THEIR PRODUCTION AND USE

The present invention relates to carbamoyltriazoles, and their production and use. More particularly, it relates to carbamoyltriazoles representable by the formula:

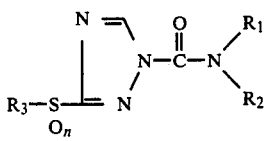
(I)

wherein $R_1$ and $R_2$ are each a lower alkyl group or they may together represent a lower alkylene group so as to form a nitrogen-containing cyclic group with the nitrogen atom to which they attach, $R_3$ is a cycloalkyl(lower)alkyl group, an oxacycloalkyl(lower)alkyl group or a dioxacycloalkyl(lower)alkyl group and n is an integer of 0 to 2, and their production and use as herbicides.

In this specification, the term "lower" is intended to mean a group having not more than eight carbon atoms, especially not more than 6 carbon atoms. The terms "cycloalkyl", "oxacycloalkyl" and "dioxacycloalkyl" are intended to mean those having not more than eight ring atoms, particularly from 3 to 6 carbon atoms.

It is known that certain kinds of carbamoyltriazoles exert a herbicidal activity. For instance, U.S. Pat. No. 3,952,001 discloses that 1-diethylcarbamoyl-3-propylsulfonyl-1,2,4-triazole, 1-diethylcarbamoyl-3-propylsulfinyl-1,2,4-triazole, 1-diethylcarbamoyl-3-propylthio-1,2,4-triazoles, etc. are useful as herbicides. However, their herbicidal activity is still not always satisfactory.

It has now been found that the carbamoyltriazoles (I) generally show a strong herbicidal activity against a wide variety of weeds including broad-leaved weeds, Graminaceous weeds and Cyperaceous weeds in agricultural plowed fields by foliar or soil treatment and do no produce any material phytotoxicity on various agricultural crops (i.e. subarbeet, corn, wheat, rice plant, soybean, cotton). Examples of broad-leaved weeds which can be controlled or exterminated by the carbamoyltriazoles (I) are wild buckwheat (*Polygonum convolvulus*), common purslane (*Portulaca oleracea*), common chickweed (*Stellaria media*), black nightshade (*Solanum nigrum*), persian speedwell (*Veronica persica*), pale smartweed (*Polygonum lapathifolium*), catchweed bedstraw (*Galium aparine*), henbit (*Lamium amplexicaure*), scentless chamomile (*Matricaria perforata*), field pansy (*Viola arvensis*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), velvetleaf (*Abutilon theophrasti*), ivyleaf morningglory (*Ipomoea hederacea*), tall morningglory (*Ipomoea purpurea*), etc. Examples of Graminaceous weeds against which the carbamoyltriazoles (I) show a herbicidal activity are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oat (*Avena fatua*), johnsongrass (*Sorghum halepense*), quackgrass (*Agropyron repens*), downy brome (*Bromus tectorum*), bermudagrass (*Cynondon dactylon*), etc. Examples of Cyperaceous weeds to which the carbamoyltriazoles (I) are applicable are rice flatsedge (*Cyperus iria*), purple nutsedge (*Cyperus rotundus*), etc.

It has also been found that the carbamoyltriazoles (I) can control or exterminate in paddy fields Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as smallflower sedge (*Cyperus difformis*), hardstem bulrush (*Scirpus juncoides*), needle spikerush (*Eleocharis acicularis*) and water nutsedge (*Cyperus serotinus*) and paddy-field weeds such as monochoria (*Monochoria vaginalis*) while exerting no material phytotoxicity to rice plants.

Accordingly, the carbamoyltriazoles (I) can be used as herbicides applicable to agricultural plowed fields as well as paddy fields without exerting any material chemical injury to crop plants. Their high selectivity to sugarbeet is particularly notable.

Among the carbamoyltriazoles (I), preferred are 3-(1,3-dioxacyclopentan-2-yl(lower)alkylsulfonyl)-1-(N,N-di(lower)alkylcarbamoyl-1,2,4-triazoles, particularly 3-[2-(1,3-dioxacyclopentan-2-yl)ethylsulfonyl]-1-(N-ethyl-N-n-propylcarbamoyl)-1,2,4-triazole.

The carbamoyltriazoles (I) may be produced by reacting a triazole of the formula:

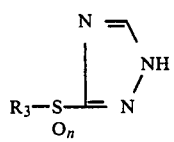
(II)

wherein $R_3$ and n are each as defined above with a carbamoyl halide of the formula:

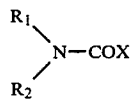
(III)

wherein $R_1$ and $R_2$ are each as defined above and X is a halogen atom in a solvent in the presence of a dehydrohalogenating agent.

The equivalent ratio of the trialzole (II), the carbamoyl halide (III) and the dehydrohalogenating agent to be used may be usually 1:1–1.5:1–10.

Examples of the solvent are aromatic hydrocarbons (e.g. benzene, toluene, xylene), halogenated hydrocarbons (e.g. chloroform, methylene chloride, chlorobenzene), ethers (e.g. diethyl ether, tetrahydrofuran), ketones (e.g. acetone, methylethylketone), orgainic bases (e.g. pyridine, triethylamine, N,N-diethylaniline), acetonitrile, N,N-dimethylformamide, dimethylsulfoxide, water, etc.

As the dehydrohalogenating agent, there may be used inorganic bases (e.g. sodium hydroxide, potassium hydroxide, sodium carbonate, potassium carbonate, sodium hydrogen carbonate), organic bases (e.g. pyridine, triethylamine, N,N-diethylaniline), etc.

The reaction may be normally carried out at a temperature between the freezing point and the boiling point of the solvent, preferably from 0° to 150° C., within a period of 10 minutes to 48 hours.

Upon completion of the reaction, the reaction mixture may be subjected to conventional post-treatment such as removal of the solvent and, if necessary, purification by recrystallization or column chromatography to produce the carbamoyltriazole (I).

When production of the carbamoyltriazoles (I) wherein n is 1 or 2 is desired, there may be alternatively adopted oxidation of carbamoyltriazoles of the formula:

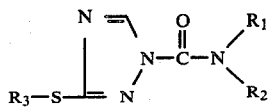

wherein $R_1$, $R_2$ and $R_3$ are each as defined above with an oxidizing agent.

Examples of the oxidizing agent are hydrogen peroxide, aromatic peracids (e.g. m-chloroperbenzoic acid), aliphatic peracids (e.g. peracetic acid, trifluoroperacetic acid), etc. In the reaction system, any solvent may be used if necessary. An appropriate solvent may be chosen depending upon the kind of the oxidizing agent. For instance, in case of using hydrogen peroxide as the oxidizing agent, water, glacial acetic acid, acetone, etc. can be favorably employed. In case of an aromatic peracid, halogenated hydrocarbons (e.g. chloroform, methylene chloride), ethers (e.g. dietyl ether, dioxane), etc. are usable. In case of an aliphatic peracid, the aliphatic peracid itself may be used in excess without using any other solvent.

The reaction is normally carried out at a temperature between the freezing point and the boiling point of the solvent, preferably from 0° to 100° C., within a period of 10 minutes to 24 hours.

Upon completion of the reaction, the reaction mixture may be subjected to conventional post-treatment such as washing with aqueous alkali and removal of the solvent and, if necessary, purification by recrystallization or column chromatography to produce the carbamoyltriazole (I).

Practical embodiments of the invention for production of the carbamoyltriazoles (I) are shown below.

EXAMPLE 1

To a solution of 3-cyclopropylmethylthio-1,2,4-triazole (3.8 g) in pyridine (30 ml), diethylcarbamoyl chloride (3.4 g) was added, and the resultant mixture was allowed to stand at room temperature for 10 hours. Water (250 ml) was added to the reaction mixture, which was then extracted with chloroform (150 ml) two times. The chloroform extract was washed with 1N hydrochloric acid (150 ml) two times and water (200 ml) one time, dried over magnesium sulfate, and concentrated under reduced pressure to give 5.2 g of 1-diethylcarbamoyl-3-cyclopropylmethylthio-1,2,4-triazole (Compound No. 1). Yield, 84%. M.P. 51°-52° C.

EXAMPLE 2

To a solution of 1-diethylcarbamoyl-3-cyclopropylmethylthio-1,2,4-triazole (2.0 g) in chloroform (100 ml), m-chloroperbenzoic acid (4.1 g; content, 70%) was added at 5° to 10° C. in 5 minutes, and the resultant mixtures was allowed to stand at room temperature for 15 hours. The resultant mixture was washed with aqueous potassium carbonate solution two times, dried over magnesium sulfate and concentrated under reduced pressure to give 2.0 g of 1-diethylcarbamoyl-3-cyclopropylmethylsulfonyl-1,2,4-triazole (Compound No. 3). Yield, 89%. $n_D^{25.5}$ 1.5162.

In the same manner as above, there can be produced the carbamoyltriazoles (I), of which some typical examples are shown in Table 1.

TABLE 1

| No. | $R_1$ | $R_2$ | $R_3$ | n | Physical constant |
|---|---|---|---|---|---|
| 1 | $C_2H_5$ | $C_2H_5$ | −CH₂CH(CH₂)(CH₂) (cyclopropylmethyl) | 0 | M.P. 51–52° C. |
| 2 | $C_2H_5$ | $C_2H_5$ | −CH₂CH(CH₂)(CH₂) | 1 | $n_D^{25}$ 1.5185 |
| 3 | $C_2H_5$ | $C_2H_5$ | −CH₂CH(CH₂)(CH₂) | 2 | $n_D^{25.5}$ 1.5162 |
| 4 | $C_2H_5$ | $C_2H_5$ | −CH₂CH(O−CH₂)(O−CH₂) | 0 | $n_D^{23}$ 1.5195 |

TABLE 1-continued $$\begin{array}{c} N \stackrel{}{=\!=\!=} \\ R_3-S \stackrel{|}{=\!=\!=} N \\ O_n \end{array} \begin{array}{c} O \\ \| \\ N-C-N \end{array} \begin{array}{c} R_1 \\ R_2 \end{array} \quad (I)$$

| No. | $R_1$ | $R_2$ | $R_3$ | n | Physical constant |
|---|---|---|---|---|---|
| 5 | $C_2H_5$ | $C_2H_5$ | $-CH_2CH\begin{array}{c}O-CH_2\\ \\O-CH_2\end{array}$ | 1 | $n_D^{24}$ 1.5210 |
| 6 | $C_2H_5$ | $C_2H_5$ | $-CH_2CH\begin{array}{c}O-CH_2\\ \\O-CH_2\end{array}$ | 2 | $n_D^{18}$ 1.5123 |
| 7 | $-(CH_2)_6-$ | | $-CH_2CH\begin{array}{c}O-CH_2\\ \\O-CH_2\end{array}$ | 0 | $n_D^{20}$ 1.5343 |
| 8 | $-(CH_2)_6-$ | | $-CH_2CH\begin{array}{c}O-CH_2\\ \\O-CH_2\end{array}$ | 2 | $n_D^{20}$ 1.5225 |
| 9 | $C_2H_5$ | $n-C_3H_7$ | $-CH_2CH\begin{array}{c}O-CH_2\\ \\O-CH_2\end{array}$ | 0 | $n_D^{27.5}$ 1.5220 |
| 10 | $C_2H_5$ | $n-C_3H_7$ | $-CH_2CH\begin{array}{c}O-CH_2\\ \\O-CH_2\end{array}$ | 1 | $n_D^{28}$ 1.5160 |
| 11 | $C_2H_5$ | $n-C_3H_7$ | $-CH_2CH\begin{array}{c}O-CH_2\\ \\O-CH_2\end{array}$ | 2 | $n_D^{28}$ 1.5033 |
| 12 | $C_2H_5$ | $n-C_3H_7$ | $-CH_2CH\begin{array}{c}CH_2\\ \\CH_2\end{array}$ | 0 | $n_D^{27}$ 1.5204 |
| 13 | $C_2H_5$ | $n-C_3H_7$ | $-CH_2CH\begin{array}{c}CH_2\\ \\CH_2\end{array}$ | 1 | $n_D^{26}$ 1.5145 |
| 14 | $C_2H_5$ | $n-C_3H_7$ | $-CH_2CH\begin{array}{c}CH_2\\ \\CH_2\end{array}$ | 2 | $n_D^{25}$ 1.5125 |
| 15 | $n-C_3H_7$ | $n-C_3H_7$ | $-CH_2-CH\begin{array}{c}CH_2\\ \\CH_2\end{array}$ | 0 | $n_D^{26.5}$ 1.5120 |
| 16 | $n-C_3H_7$ | $n-C_3H_7$ | $-CH_2-CH\begin{array}{c}CH_2\\ \\CH_2\end{array}$ | 1 | $n_D^{26.5}$ 1.5070 |

TABLE 1-continued $$\underset{R_3-S\underset{O_n}{\overset{\|}{=}}}{\overset{N=}{\underset{N}{\bigvee}}}\overset{O}{\underset{\|}{C}}\overset{R_1}{\underset{R_2}{N}}\quad(I)$$

| No. | R₁ | R₂ | R₃ | n | Physical constant |
|---|---|---|---|---|---|
| 17 | n-$C_3H_7$ | n-$C_3H_7$ | $-CH_2-CH\overset{CH_2}{\underset{CH_2}{<}}$ | 2 | M.P. 66–67° C. |
| 18 | $C_2H_5$ | $C_2H_5$ | $-CH_2CH_2CH\overset{O-CH_2}{\underset{O-CH_2}{<}}$ | 0 | $n_D^{27}$ 1.5175 |
| 19 | $C_2H_5$ | $C_2H_5$ | $-CH_2CH_2CH\overset{O-CH_2}{\underset{O-CH_2}{<}}$ | 1 | $n_D^{27}$ 1.5110 |
| 20 | $C_2H_5$ | $C_2H_5$ | $-CH_2CH_2CH\overset{O-CH_2}{\underset{O-CH_2}{<}}$ | 2 | $n_D^{27}$ 1.5030 |
| 21 | $C_2H_5$ | n-$C_3H_7$ | $-CH_2CH_2CH\overset{O-CH_2}{\underset{O-CH_2}{<}}$ | 0 | $n_D^{25.5}$ 1.5170 |
| 22 | $C_2H_5$ | n-$C_3H_7$ | $-CH_2CH_2CH\overset{O-CH_2}{\underset{O-CH_2}{<}}$ | 1 | $n_D^{24.5}$ 1.5156 |
| 23 | $C_2H_5$ | n-$C_3H_7$ | $-CH_2CH_2CH\overset{O-CH_2}{\underset{O-CH_2}{<}}$ | 2 | $n_D^{23.5}$ 1.5010 |
| 24 | n-$C_3H_7$ | n-$C_3H_7$ | $-CH_2CH_2CH\overset{O-CH_2}{\underset{O-CH_2}{<}}$ | 0 | $n_D^{25.5}$ 1.5065 |
| 25 | n-$C_3H_7$ | n-$C_3H_7$ | $-CH_2CH_2CH\overset{O-CH_2}{\underset{O-CH_2}{<}}$ | 1 | $n_D^{24.5}$ 1.5015 |
| 26 | n-$C_3H_7$ | n-$C_3H_7$ | $-CH_2CH_2CH\overset{O-CH_2}{\underset{O-CH_2}{<}}$ | 2 | $n_D^{23.5}$ 1.4982 |
| 27 | $C_2H_5$ | n-$C_3H_7$ | $-(CH_2)_3CH\overset{O-CH_2}{\underset{O-CH_2}{<}}$ | 0 | $n_D^{24}$ 1.5050 |
| 28 | $C_2H_5$ | n-$C_3H_7$ | $-(CH_2)_3CH\overset{O-CH_2}{\underset{O-CH_2}{<}}$ | 1 | $n_D^{25}$ 1.5100 |

TABLE 1-continued

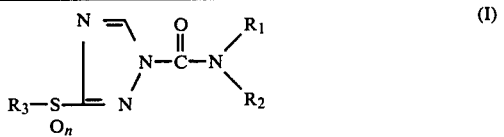

(I)

| No. | $R_1$ | $R_2$ | $R_3$ | n | Physical constant |
|-----|-------|-------|-------|---|-------------------|
| 29 | $C_2H_5$ | $n\text{-}C_3H_7$ | $-(CH_2)_3CH\begin{smallmatrix}O-CH_2\\ \\O-CH_2\end{smallmatrix}$ | 2 | $n_D^{25}$ 1.4880 |
| 30 | $C_2H_5$ | $C_2H_5$ | $-(CH_2)_3CH\begin{smallmatrix}O-CH_2\\ \\O-CH_2\end{smallmatrix}$ | 0 | $n_D^{26}$ 1.5200 |
| 31 | $C_2H_5$ | $C_2H_5$ | $-(CH_2)_3CH\begin{smallmatrix}O-CH_2\\ \\O-CH_2\end{smallmatrix}$ | 1 | $n_D^{25}$ 1.5130 |
| 32 | $C_2H_5$ | $C_2H_5$ | $-(CH_2)_3CH\begin{smallmatrix}O-CH_2\\ \\O-CH_2\end{smallmatrix}$ | 2 | $n_D^{24}$ 1.5020 |
| 33 | $C_2H_5$ | $C_2H_5$ | $-CH_2CH_2CH_2C(CH_3)\begin{smallmatrix}O-CH_2\\ \\O-CH_2\end{smallmatrix}$ | 2 | $n_D^{24}$ 1.4995 |
| 34 | $C_2H_5$ | $C_2H_5$ | $-CH_2CH_2CH\begin{smallmatrix}O-CH_2\\ \phantom{O}\diagdown CH_2\\O-CH_2\end{smallmatrix}$ | 0 | $n_D^{26}$ 1.5212 |
| 35 | $C_2H_5$ | $C_2H_5$ | $-CH_2CH_2CH\begin{smallmatrix}O-CH_2\\ \phantom{O}\diagdown CH_2\\O-CH_2\end{smallmatrix}$ | 1 | $n_D^{26}$ 1.5120 |
| 36 | $C_2H_5$ | $C_2H_5$ | $-CH_2CH_2CH\begin{smallmatrix}O-CH_2\\ \phantom{O}\diagdown CH_2\\O-CH_2\end{smallmatrix}$ | 2 | $n_D^{25.5}$ 1.5000 |
| 37 | $C_2H_5$ | $n\text{-}C_3H_7$ | $-CH_2CH_2CH\begin{smallmatrix}O-CH_2\\ \phantom{O}\diagdown CH_2\\O-CH_2\end{smallmatrix}$ | 0 | $n_D^{25}$ 1.5133 |
| 38 | $C_2H_5$ | $n\text{-}C_3H_7$ | $-CH_2CH_2CH\begin{smallmatrix}O-CH_2\\ \phantom{O}\diagdown CH_2\\O-CH_2\end{smallmatrix}$ | 1 | $n_D^{26}$ 1.5240 |
| 39 | $C_2H_5$ | $n\text{-}C_3H_7$ | $-CH_2CH_2CH\begin{smallmatrix}O-CH_2\\ \phantom{O}\diagdown CH_2\\O-CH_2\end{smallmatrix}$ | 2 | $n_D^{25.5}$ 1.4985 |

The starting triazole (II) wherein n is 0 can be produced by reacting a halide of the formula:

$$R_3-Y \qquad (IV)$$

wherein R₃ is defined above and Y is a halogen atom with 3-mercapto-1,2,4-triazole in a solvent in the presence of a dehydrohalogenating agent at a temperature of 0° to 150° C. for a period of 10 minutes to 24 hours. The equivalent ratio of the halide (IV), 3-mercapto-1,2,4-triazole and the dehydrohalogenating agent may be 1:0.9–1.2:1–10. Examples of the solvent are aromatic hydrocarbons (e.g. benzene, toluene, xylene), halogenated hydrocarbons (e.g. chloroform, methylene chloride, chlorobenzene), ethers (e.g. diethyl ether, tetrahydrofuran), ketones (e.g. acetone, methylethylketone), organic bases (e.g. pyridine, triethylamine, N,N-diethylaniline), acetonitrile, N,N-dimethylformamide, dimethylsulfoxide, water, etc. As the dehydrohalogenating agent, there may be used inorganic bases (e.g. sodium hydroxide, potassium hydroxide, sodium carbonate, potassium carbonate, sodium bicarbonate), alkali metal alkoxides (e.g. sodium methoxide, potassium ethoxide), organic bases (e.g. pyridine, triethylamine, N,N-diethylaniline), etc.

Upon completion of the reaction, the reaction mixture may be subjected to conventional post-treatment such as removal of the solvent and, if necessary, purification by recrystallization or column chromatography to produce the triazole (II) wherein n is 0.

The triazole (II) wherein n is 1 or 2 may be produced by subjecting the triazole (II) wherein n is 0 to oxidation with an oxidizing agent. Examples of the oxidizing agent are hydrogen peroxide, aromatic peracids (e.g. m-chloroperbenzoic acid), aliphatic peracids (e.g. peracetic acid, trifluoroperacetic acid), etc. When desired, a solvent may be employed, and an appropriate solvent may be chosen depending upon the kind of the oxidizing agent. For instance, in case of using hydrogen peroxide as the oxidizing agent, water, glacial acetic acid, acetone, etc. are favorably used. In case of an aromatic peracid, halogenated hydrocarbons (e.g. chloroform, methylene chloride), ethers (e.g. dietyl ether, dioxane), etc. are preferably used. In case of an aliphatic peracid, the aliphatic peracid itself may be used in excess without any other solvent. The reaction is ordinarily carried out at a temperature between the freezing point and the boiling point of the solvent, preferably from 0° to 100° C., within a period of 10 minutes to 24 hours.

Upon completion of the reaction, the reaction mixture may be subjected to conventional post-treatment such as washing with aqueous alkali and removal of the solvent and, if necessary, purification by recrystallization or column chromatography to produce the triazole (II) wherein n is 1 or 2.

A typical example for production of the triazoles (II) is shown below.

REFERENCE EXAMPLE 1

To a solution of 3-mercapto-1,2,4-triazole (7.1 g) and sodium methoxide (3.8 g) in methanol (100 ml), there was added cyclopropylmethyl bromide (9.5 g), and the resultant mixture was allowed to stand at room temperature for 10 hours. After removal of the solvent, the residue was extracted with chloroform. Evaporation of the chloroform extract gave 10.8 g of 3-cyclopropylmethylthio-1,2,4-triazole. Yield, 99%. M.P., 69°–70° C.

On the practical usage of the carbamoyltriazole (I) as a herbicide, it may be applied as such or preferably in any preparation form (e.g. emulsifiable concentrate, wettable powder, suspension, granules) in combination with an inert carrier such as solid or liquid carrier or diluent and optionally any other additive such as a surface active agent and an auxiliary agent.

The content of the carbamoyltriazole (I) as the active ingredient in said preparation form may be usually within a range of 0.1 to 90% by weight, preferably of 1 to 80% by weight.

Examples of the solid carrier or diluent are fine powders or granules of kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, celosolve), ketones (e.g. acetone, cyclohexanone, isophorone), plant oils (e.g. soybean oil, cotton seed oil), dimethylsulfoxide, acetonitrile, water, etc. The surface active agent usable for emulsifying, dispersing or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agent include ligninsulfonates, alginates, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

FORMULATION EXAMPLE 1

Fifty parts of Compound No. 1, 3 parts of calcium ligninsulfonate, 2 parts of sodium laurylsulfate and 45 parts of synthetic hydrated silicon dioxide are well mixed to obtain a wettable powder.

FORMULATION EXAMPLE 2

Two parts of Compound No. 3, 14 parts of polyoxyethylenestyrylphenyl ether, 6 parts of calcium dodecylbenzenesulfonate and 78 parts of isophorone are well mixed to obtain an emulsifiable concentrate.

FORMULATION EXAMPLE 3

Two parts of Compound No. 6, 1 part of synthetic hydrated silicon dioxide, 2 parts of calcium ligninsulfonate, 30 parts of bentonite and 65 parts of kaolin clay are well mixed. The mixture is then kneaded with water, granulated and dried to obtain granules.

FORMULATION EXAMPLE 4

Twenty-five parts of Compound No. 14 is mixed with 3 parts of polyoxyethylene sorbitan monooleate, 3 parts of CMC (carboxymethyl cellulose) and 69 parts of water, and the mixture is pulverized until the particle size becomes less than 5 microns to obtain a suspension.

The carbamoyltriazoles (I) thus formulated is useful for the pre-emergence or post-emergence control of undersired weeds by soil or foliar treatment as well as flood fallowing treatment. These treatments include the application to the soil surface prior to or after the transplanting or the incorporation into the soil. The foliar treatment may be effected by spraying the herbicidal composition containing the carbamoyltriazole (I) over the top of plants. It may also be applied directly to weeds with care so as to keep the chemical off the crop foliage.

The carbamoyltriazoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Besides, the carbamoyltriazoles (I) can be used as herbicides applicable to agricultural plowed field as well as paddy field. They are also useful as herbicides to be employed for orchard, pasture land, forest, non-agricultural field, etc.

The dosage rate of the carbamoyltriazoles (I) may vary on prevailing weather conditions, preparation used, prevailing season, mode of application, soil involved, crop and weed species, etc. Generally, however, the dosage rate may be from 0.5 to 200 grams, preferably from 1 to 100 grams, of the active ingredient per are. The herbicidal composition of the present invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as stated above, polyoxyethylene resin acid esters, ligninsulfonates, abietates, dinaphthylmethanedisulfonates, paraffin, etc. The composition prepared in the form of granules may be normally applied as such without dilution.

The biological effect of the carbamoyltriazoles (I) as herbicides are illustratively shown in the following Examples wherein the phytotoxicity to crop plants and the herbicidal activity on weeds were observed visually as to the degree of germination as well as the growth inhibition and rated with an index of 0, 1, 2, 3, 4 or 5, in which the numeral "0" indicates that no material difference is seen in comparison with the untreated plants and the numeral "5" indicates the complete inhibition or death of the test plants.

The compounds shown in Table 2 below were used for comparison.

TABLE 2

| Compound No. | Structure | Remarks |
|---|---|---|
| A | n-C$_3$H$_7$—S(O$_2$)— triazole —N—C(O)—N(C$_2$H$_5$)$_2$ | U.S. Pat. No. 3,952,001 |
| B | n-C$_3$H$_7$—S(O)— triazole —N—C(O)—N(C$_2$H$_5$)$_2$ | U.S. Pat. No. 3,952,001 |
| C | n-C$_3$H$_7$—S— triazole —N—C(O)—N(C$_2$H$_5$)$_2$ | U.S. Pat. No. 3,952,001 |

TABLE 2-continued

| Compound No. | Structure | Remarks |
|---|---|---|
| D | 2,6-diethylphenyl-N(CH$_2$OCH$_3$)(COCH$_2$Cl) | Commercially available herbicide; "alachlor" |
| E | 2-chloro-4-(isopropylamino)-6-(ethylamino)-1,3,5-triazine | Commercially available herbicide; "atrazine" |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designed amount of the test compound formulated into an emulsifiable concentrate according to Formulation Example 2 was diluted with water, and the dilution was sprayed onto the soil surface by means of a small hand sprayer at a spray volume of 10 liters per are, followed by mixing the soil surface in a depth of 4 cm. Thereafter, the test plants were grown in a greenhouse for 20 days, and the herbicidal activity was examined. The results are shown in Table 3.

TABLE 3

| | | Herbicidal activity | | | |
|---|---|---|---|---|---|
| Compound No. | Dosage (g/are) | Japanese millet | Oats | Tall morning-glory | Velvet-leaf |
| 1 | 80 | 5 | 5 | 4 | 4 |
| 2 | 80 | 5 | 5 | 4 | 5 |
| 3 | 80 | 5 | 5 | 5 | 5 |
| 5 | 80 | 5 | 2 | 4 | 5 |
| 6 | 80 | 5 | 5 | 5 | 5 |
| 10 | 80 | 5 | 2 | 4 | 3 |
| 11 | 80 | 5 | 5 | 5 | 5 |
| 13 | 80 | 5 | 4 | 3 | 2 |
| 14 | 80 | 5 | 5 | 5 | 5 |
| 16 | 80 | 5 | 4 | 3 | 2 |
| 17 | 80 | 5 | 5 | 5 | 5 |
| 23 | 80 | 5 | 4 | 5 | 5 |
| 26 | 80 | 5 | 3 | 5 | 5 |
| 29 | 80 | 5 | 5 | 4 | 5 |
| 31 | 80 | 5 | 3 | 3 | 2 |
| 32 | 80 | 5 | 5 | 4 | 3 |
| 33 | 80 | 5 | 4 | 3 | 2 |
| 35 | 80 | 5 | 4 | 5 | 5 |
| 36 | 80 | 5 | 5 | 5 | 3 |
| 38 | 80 | 5 | 4 | 3 | 5 |
| 39 | 80 | 5 | 5 | 5 | 5 |

TEST EXAMPLE 2

Vats (33 cm×23 cm×11 cm) were filled with upland field soil, and the seeds of soybean, cotton and corn as well as the seeds of velvetleaf, common chickweed, green foxtail, large crabgrass, johnsongrass and barnyardgrass (*Echinochloa crus-galli*) were sowed therein at a depth of 1 to 2 cm. A designed amount of the test compound formulated into an emulsifiable concentrate according to Formulation Example 2 was diluted with water, and the dilution was sprayed to the soil surface by means of a small hand sprayer at a spray volume of 10 liters per are. Thereafter, the test plants were grown in a greenhouse for 20 days, and the herbicidal activity was examined. The results are shown in Table 4.

TABLE 4

| Compound No. | Dosage (g/are) | Herbicidal activity | | | | | | | |
|---|---|---|---|---|---|---|---|---|---|
| | | Soybean | Cotton | Corn | Velvetleaf | Common chickweed | Green foxtail | Large crabgrass | Johnsongrass | Barnyardgrass |
| 3 | 10 | 3 | 2 | 2 | 5 | 5 | 5 | 5 | 5 | 5 |
|  | 5 | 2 | 1 | 1 | 4 | 4 | 5 | 5 | 5 | 5 |
|  | 2.5 | 0 | 0 | 0 | 3 | 3 | 4 | 5 | 5 | 4 |
| 14 | 10 | 2 | 1 | 1 | 5 | 5 | 5 | 5 | 5 | 5 |
|  | 5 | 1 | 0 | 0 | 4 | 4 | 5 | 5 | 5 | 5 |
|  | 2.5 | 0 | 0 | 0 | 2 | 3 | 4 | 5 | 4 | 4 |
| A | 10 | 4 | 3 | 4 | 4 | 4 | 5 | 5 | 5 | 5 |
|  | 5 | 2 | 2 | 3 | 3 | 3 | 4 | 5 | 4 | 4 |
|  | 2.5 | 1 | 2 | 2 | 2 | 1 | 2 | 3 | 3 | 3 |
| D | 10 | 0 | 1 | 1 | 2 | 5 | 5 | 5 | 4 | 5 |
|  | 5 | 0 | 0 | 0 | 0 | 5 | 5 | 4 | 3 | 5 |
|  | 2.5 | 0 | 0 | 0 | 0 | 3 | 4 | 3 | 1 | 4 |

TEST EXAMPLE 3

Cylindrical plastic pots (diameter, 10 cm; height, 10 cm) were filled with upland field soil, and the seeds of Japanese millet, oats, radish and velvetleaf were sowed therein and cultivated in a greenhouse for 10 days. A designed amount of the test compound formulated into an emulsifiable concentrate according to Formulation Example 2 was diluted with water containing a spreading agent, and the dilution was sprayed onto the foilage of the test plants by means of a small hand sprayer at a spray volume of 10 liters per are. Thereafter, the test plants were further grown in the greenhouse for 20 days, and the herbicidal activity was examined. The results are shown in Table 5.

TABLE 5

| Compound No. | Dosage (g/are) | Herbicidal activity | | | |
|---|---|---|---|---|---|
| | | Japanese millet | Oats | Radish | Velvetleaf |
| 3 | 40 | 4 | 4 | 3 | 2 |
| 6 | 40 | 5 | 4 | 4 | 3 |
| 10 | 40 | 4 | 4 | 5 | 3 |
| 11 | 40 | 4 | 3 | 3 | 4 |
| 12 | 40 | 3 | 2 | 5 | 3 |
| 13 | 40 | 4 | 2 | 5 | 4 |
| 14 | 40 | 4 | 4 | 5 | 4 |
| 17 | 40 | 4 | 3 | 4 | 3 |
| 23 | 40 | 4 | 2 | 4 | 5 |
| 29 | 40 | 4 | 4 | 3 | 4 |
| 32 | 40 | 4 | 4 | 2 | 4 |
| A | 40 | 4 | 2 | 0 | 2 |
| B | 40 | 4 | 0 | 0 | 0 |
| C | 40 | 0 | 0 | 0 | 0 |

TEST EXAMPLE 4

Vats (33 cm×23 cm×11 cm) were filled with upland field soil, and the seeds of corn and wheat as well as the seeds of large crabgrass, green foxtail and barnyardgrass (*Echinochloa crus-galli*) were sowed therein and cultivated in a greenhouse for 18 days. A designed amount of the test compound formulated into an emulsifiable concentrate according to Formulation Example 2 was diluted with water containing a spreading agent, and the dilution was sprayed onto the foliage of the test plants by means of a small hand sprayer at a spray volume of 5 liters per are. At the time of the application, the growing stage of the test plants varied depending on their species, but they were generally at the 2 to 4 leaf stage and in a height of 2 to 12 cm. The test plants were further grown in a greenhouse for 20 days, and the herbicidal activity was examined. The results are shown in Table 6.

TABLE 6

| Compound No. | Dosage (g/are) | Herbicidal activity | | | | |
|---|---|---|---|---|---|---|
| | | Corn | Wheat | Large crabgrass | Green foxtail | Barnyardgrass |
| 6 | 20 | 0 | 1 | 5 | 5 | 5 |
|  | 10 | 0 | 1 | 4 | 5 | 4 |
| 20 | 10 | — | 0 | 5 | 4 | 4 |
|  | 5 | — | 0 | 4 | 4 | 4 |
| 39 | 20 | — | 1 | 5 | 5 | 5 |
|  | 10 | 1 | 1 | 4 | 4 | 4 |
| A | 20 | 2 | 2 | 3 | 4 | 3 |
|  | 10 | 1 | 1 | 2 | 3 | 2 |
| E | 10 | 0 | 4 | 3 | 4 | 4 |
|  | 5 | 0 | 3 | 1 | 2 | 3 |

TEST EXAMPLE 5

Cylindrical plastic pots (diameter, 8 cm; height, 12 cm) were filled with paddy field soil, and the seeds of barnyardgrass (*Echinochloa oryzicola*), broad-leaved weeds (i.e. common falsepimpernel, indian toothcup, waterwort) and hardstem bulrush were sowed therein at a depth of 1 to 2 cm. After flooding the pots with water, rice seedlings at the 2-leaf stage were transplanted therein. Cultivation was carried out in a greenhouse. Six days thereafter, a designed amount of the test compound formulated into an emulsifiable concentrate according to Formulation Example 2 was diluted with water (5 ml), and the dilution was applied to the pots by perfusion. The test plants were grown for further 20 days in the greenhouse, and the herbicidal activity was examined. The results are shown in Table 7.

TABLE 7

| Compound No. | Dosage (g/are) | Herbicidal activity | | | |
|---|---|---|---|---|---|
| | | Rice plant | Barnyardgrass | Broad-leaved weed | Hardstem bulrush |
| 1 | 10 | 0 | 5 | 5 | 2 |
| 6 | 10 | 2 | 5 | 5 | 4 |
|  | 2.5 | 0 | 5 | 4 | 2 |
| 8 | 10 | 1 | 4 | 5 | 4 |
| 16 | 10 | 0 | 5 | 4 | 3 |
| 17 | 10 | 0 | 5 | 5 | 4 |
| 26 | 10 | — | 5 | 5 | 5 |
|  | 2.5 | 0 | 5 | 4 | 4 |
| 29 | 10 | 0 | 5 | 5 | 4 |
| 39 | 10 | 0 | 5 | 4 | 4 |

TEST EXAMPLE 6

Vats (33 cm×23 cm×11 cm) were filled with upland field soil, and the seeds of sugarbeet as well as the seeds of black nightshade, common lambsquarters, wild mustard, field pansy, common chickweed, blackgrass and annual bluegrass were sowed therein at a depth of 1 to 2 cm. A designed amount of the test compound formulated into an emulsifiable concentrate according to Formulation Example 2 was diluted with water, and the dilution was sprayed to the soil surface by means of a small hand sprayer at a spray volume of 10 liters per are. Thereafter, the test plants were grown in a greenhouse for 27 days, and the herbicidal activity was examined. The results are shown in Table 8.

TABLE 8

| Compound No. | Dosage (g/are) | Herbicidal activity | | | | | | | |
|---|---|---|---|---|---|---|---|---|---|
| | | Sugar-beet | Black night-shade | Common lambs-quarters | Wild mustard | Field pansy | Common chick-weed | Black-grass | Annual bluegrass |
| 23 | 10 | 1 | 5 | 5 | 5 | 5 | 5 | 5 | 5 |
|  | 5 | 0 | 4 | 5 | 5 | 4 | 5 | 5 | 5 |
| 26 | 10 | 0 | 5 | 5 | 4 | 4 | 5 | 4 | 5 |
| 39 | 10 | 0 | 5 | 5 | 5 | — | 5 | 5 | 5 |
|  | 5 | 0 | 5 | 4 | 4 | — | 5 | 4 | — |
| D | 10 | 4 | 4 | 5 | 3 | 3 | 4 | 3 | 4 |
|  | 5 | 3 | 2 | 2 | 1 | 1 | 2 | — | 4 |

What is claimed is:

1. A compound of the formula:

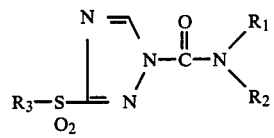

wherein $R_1$ and $R_2$ are each a lower alkyl group and $R_3$ is a 1,3-dioxacyclopentan-2-yl(lower)alkyl group.

2. The compound according to claim 1, of the formula:

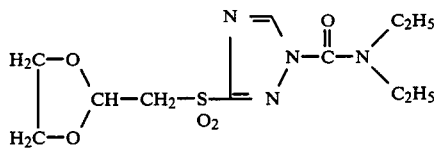

3. The compound according to claim 1, of the formula:

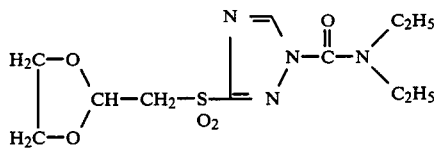

4. A herbicidal composition which comprises as an active ingredient a herbicidally effective amount of a compound of the formula:

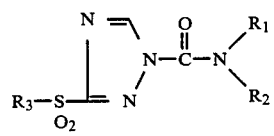

wherein $R_1$ and $R_2$ are each a lower alkyl group and $R_3$ is a 1,3-dioxacyclopentan-2-yl(lower)alkyl group and an inert carrier or diluent.

5. A method of controlling weeds which comprises applying a herbicidally effective amount of a compound of the formula:

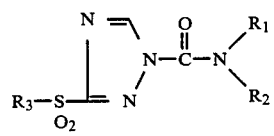

wherein $R_1$ and $R_2$ are each a lower alkyl group and $R_3$ is a 1,3-dioxacyclopentan-2-yl(lower)alkyl group to the area where the weeds grow or will grow.

* * * * *